(12) United States Patent
Plaxco et al.

(10) Patent No.: US 12,257,050 B2
(45) Date of Patent: Mar. 25, 2025

(54) CALIBRATION FREE IN-VIVO MEASUREMENT OF ANALYTES USING ELECTROCHEMICAL SENSORS

(71) Applicant: THE REGENTS OF THE UNIVERSITY OF CALIFORNIA, Oakland, CA (US)

(72) Inventors: Kevin Plaxco, Santa Barbara, CA (US); Netzahualcoyotl Arroyo Curras, Baltimore, MD (US)

(73) Assignee: The Regents of the University of California, Oakland, CA (US)

(*) Notice: Subject to any disclaimer, the term of this patent is extended or adjusted under 35 U.S.C. 154(b) by 603 days.

(21) Appl. No.: 16/756,681

(22) PCT Filed: Oct. 29, 2018

(86) PCT No.: PCT/US2018/058020
§ 371 (c)(1),
(2) Date: Apr. 16, 2020

(87) PCT Pub. No.: WO2019/089465
PCT Pub. Date: May 9, 2019

(65) Prior Publication Data
US 2021/0196161 A1 Jul. 1, 2021

Related U.S. Application Data

(60) Provisional application No. 62/578,665, filed on Oct. 30, 2017.

(51) Int. Cl.
*A61B 5/1473* (2006.01)
*A61B 5/00* (2006.01)
*A61B 5/145* (2006.01)

(52) U.S. Cl.
CPC ........ *A61B 5/14735* (2013.01); *A61B 5/1451* (2013.01); *A61B 5/14517* (2013.01);
(Continued)

(58) Field of Classification Search
CPC .............. A61B 5/14735; A61B 5/1451; A61B 5/14517; A61B 5/14546; A61B 5/4277;
(Continued)

(56) References Cited

U.S. PATENT DOCUMENTS 5,470,484 A * 11/1995 McNeel ................. G01N 33/18
324/439
2007/0020641 A1 1/2007 Heeger et al.
(Continued)

FOREIGN PATENT DOCUMENTS

CN 104919312 A 9/2015
CN 111683592 A 9/2020
(Continued)

OTHER PUBLICATIONS

International Preliminary Report on Patentability for International Application PCT/US2018/058020, Report issued May 5, 2020, Mailed on May 14, 2020, 5 Pgs.
(Continued)

*Primary Examiner* — Christian Jang
(74) *Attorney, Agent, or Firm* — KPPB LLP

(57) ABSTRACT

Typical electrochemical sensors measure target-induced changes in current output. Such measures of target binding are inconsistent across individual sensors, and furthermore, signal will drift over time when the sensor is deployed for long periods. These shortcomings can be avoided by the novel use of chronoamperometry to measure current decay kinetics as the indicator of target binding. Current decay lifetimes will vary in a concentration dependent manner, but remain stable across individual sensors and over time,
(Continued)

allowing for calibration-free operation. By these methods, aptamer based electrochemical sensors and other sensor types may be deployed in vivo for extended periods of time and will provide accurate measurement of target binding without calibration.

19 Claims, 8 Drawing Sheets

(52) U.S. Cl.
CPC ........ *A61B 5/14546* (2013.01); *A61B 5/4277* (2013.01); *A61B 5/4866* (2013.01); *A61B 2503/40* (2013.01)

(58) Field of Classification Search
CPC .............. A61B 5/4866; A61B 2503/40; A61B 5/14507; A61B 2560/0223; A61B 5/1495; A61B 5/7225; A61B 5/1473; A61B 5/6852; A61B 5/24; G01N 33/54386; G01N 33/5308; G01N 33/5438; G01N 33/54373

See application file for complete search history.

(56) References Cited

U.S. PATENT DOCUMENTS

| | | | |
|---|---|---|---|
| 2007/0299617 A1 | 12/2007 | Willis | |
| 2009/0068754 A1 | 3/2009 | Wu et al. | |
| 2009/0076738 A1 | 3/2009 | Kayihan et al. | |
| 2009/0194432 A1 | 8/2009 | Deng | |
| 2009/0298104 A1* | 12/2009 | Liu | A61B 5/1486 435/14 |
| 2010/0270178 A1* | 10/2010 | Guo | A61B 5/1486 205/777.5 |
| 2012/0123690 A1 | 5/2012 | Wang et al. | |
| 2012/0267255 A1* | 10/2012 | Yau | G01N 27/3277 205/687 |
| 2015/0126391 A1 | 5/2015 | Umek et al. | |
| 2015/0176054 A1 | 6/2015 | Wu et al. | |
| 2015/0276650 A1 | 10/2015 | Chen et al. | |
| 2015/0377821 A1 | 12/2015 | Varney et al. | |
| 2016/0113996 A1* | 4/2016 | Moqrich | A61P 29/00 800/9 |
| 2016/0166186 A1 | 6/2016 | Ferguson et al. | |
| 2018/0195996 A1* | 7/2018 | Wang | G01N 27/416 |

FOREIGN PATENT DOCUMENTS

| | | |
|---|---|---|
| EP | 1770396 A2 | 4/2007 |
| JP | 2007108171 A | 4/2007 |
| JP | 2010507808 A | 3/2010 |
| JP | 2010534838 A | 11/2010 |
| WO | WO1995019566 A1 | 7/1995 |
| WO | 2008051742 A2 | 5/2008 |
| WO | 2009015316 A1 | 1/2009 |
| WO | 2017007826 A1 | 1/2017 |
| WO | 2019089465 A1 | 5/2019 |

OTHER PUBLICATIONS

International Search Report and Written Opinion for International Application PCT/US2018/058020, search completed Mar. 8, 2019, Mailed Mar. 11, 2019, 8 Pgs.

Cash et al., "An Electrochemical Sensor for the Detection of Protein-Small Molecule Interactions Directly in Serum and Other Complex Matrices", Journal of the American Chemical Society, vol. 131, No. 20, May 27, 2009, 8 Pgs.

Extended European Search Report for European Application No. 18874074.0, Search Completed Jul. 2, 2021, Mailed Jul. 12, 2021, 9 Pgs.

Feld et al., "Trinuclear Ruthenium Clusters as Bivalent Electrochemical Probes for Ligand-Receptor Binding Interactions", Langmuir, vol. 28, No. 1, Jan. 10, 2012, 29 pgs, doi: 10.1021/la202882k.

Ge et al., "A Robust Electronic Switch Made of Immobilized Duplex/Quadruplex DNA", Agnewandte Chemie International Edition, vol. 49, Nov. 23, 2010, pp. 9965-9967, doi: 10.1002/anie.201004946.

Kamman et al., "Multi-Exponential Relaxation Analysis with MR Imaging and NMR Spectroscopy Using Fat-Water Systems", Magnetic Resonance Imaging, vol. 5, No. 5, 1987, pp. 381-392, doi: 10.1016/0730-725X(87)90127-5.

Katayama et al., "The Design of Cyclic AMP—Recognizing Oligopeptides and Evaluation of Its Capability for Cyclic AMP Recognition Using an Electrochemical System", Analytical Chemistry, vol. 72, No. 19, Oct. 1, 2000, pp. 4671-4674, doi: 10.1021/ac990847h.

Le Floch et al., "Label-Free Electrochemical Detection of Protein Based on a Ferrocene-Bearing Cationic Polythiophene and Aptamer", Analytical Chemistry, vol. 78, No. 13, Jun. 8, 2006, pp. 4727-4731, doi: 10.1021/ac0521955.

Plumb et al., "Interaction of a Ferrocenoyl-Modified Peptide with Papain: Toward Protein-Sensitive Electrochemical Probes", Bioconjugate Chemistry, vol. 14, No. 3, May 7, 2003, pp. 601-606, doi: 10.1021/bc0256446.

Prasad et al., "The Role of Ligand Displacement in Sm(II)-HMPA-Based Reductions", Journal of the American Chemical Society, vol. 126, No. 22, May 11, 2004, pp. 6891-6894, doi: 10.1021/ja049161j.

Sander et al., "Electrochemical Analyses of Redox-Active Iron Minerals: A Review of Nonmediated and Mediated Approaches", Environmental Science & Technology, vol. 49, Apr. 9, 2015, pp. 5862-5878, doi: 10.1021/acs.est.5b00006.

* cited by examiner

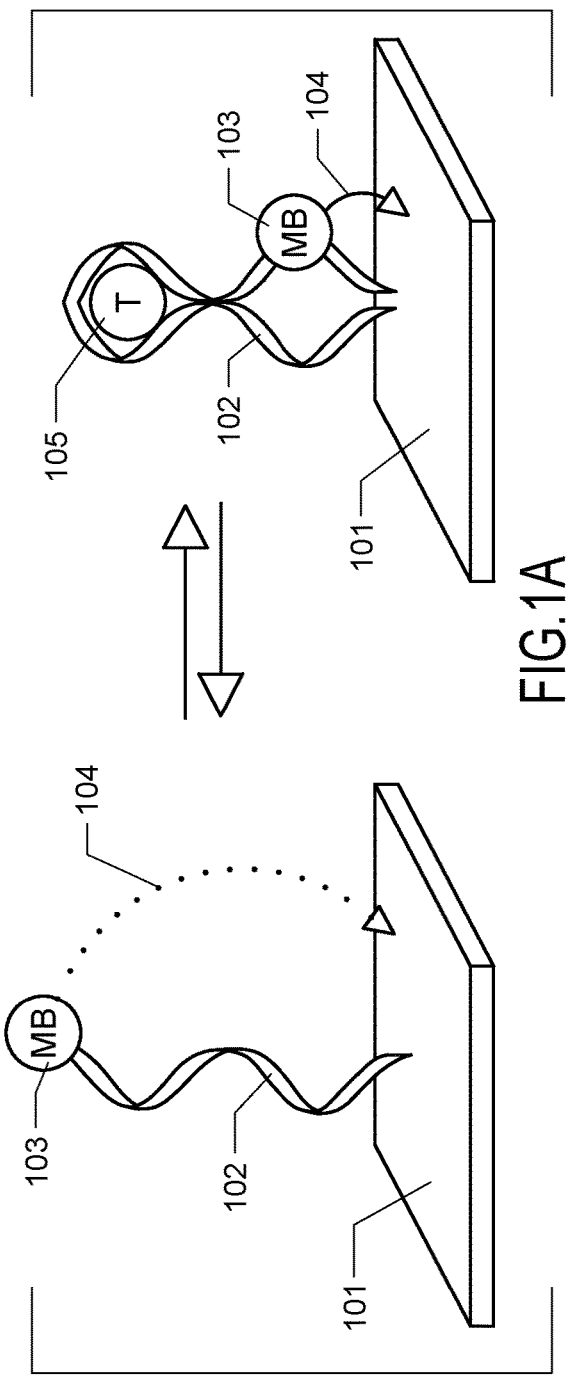
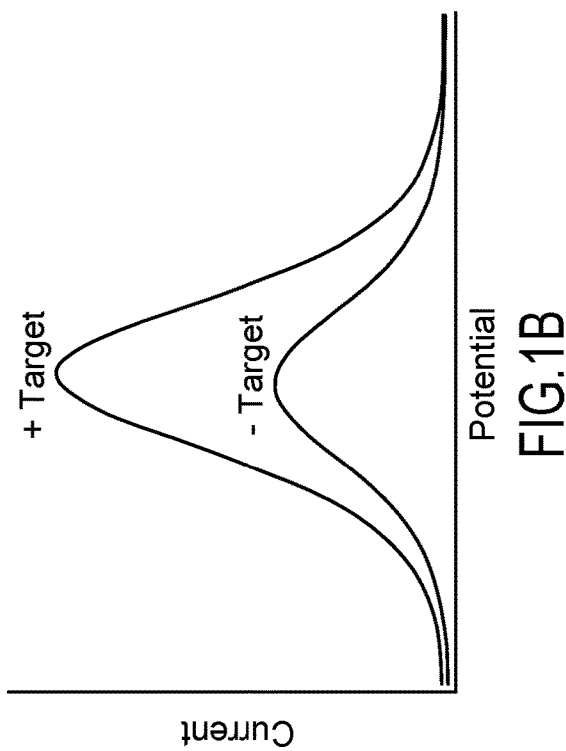
FIG.1A
FIG.1B

CALIBRATION FREE IN-VIVO MEASUREMENT OF ANALYTES USING ELECTROCHEMICAL SENSORS

CROSS-REFERENCE TO RELATED APPLICATIONS

This application claims priority to International Application No. PCT/US2018/058020, entitled "Calibration Free In-vivo Measurement of Analytes Using Electrochemical Sensors," filed on Oct. 29, 2018, which claims priority to U.S. Provisional Application No. 62/578,665, entitled "Calibration Free In-Vivo Measurement of Analytes Using Electrochemical Sensors," filed on Oct. 30, 2017, each of which is incorporated by reference herein in its entirety.

STATEMENT REGARDING FEDERALLY SPONSORED RESEARCH OR DEVELOPMENT

This invention was made with government support under grant number W911NF-09-0001 U.S. Army Research Office awarded by the U.S. Army Research Office. The government has certain rights in the invention.

FIELD OF INVENTION

The current disclosure is directed to systems and methods for calibration free electrochemical sensors; and more particularly to calibration free measurements of analytes using electrochemical sensors.

BACKGROUND OF THE INVENTION

Various types of electrochemical sensors for the detection of target molecules are known. Many such sensors produce a current output, wherein the magnitude of the current output changes in response to binding of the target molecule. Electrochemical aptamer-based (EA-B) sensors use redox-reporter-modified, electrode-bound aptamers, wherein binding-induced conformational changes in the aptamer result in measurable changes in electron flows between the redox reporter and electrode. EA-B sensors have provided the art with a versatile platform for the measurement of target analytes in complex samples. EA-B sensors have even been demonstrated to work in vivo for the real-time detection of drugs and other target species in flowing whole blood. However, despite the great potential of this platform, E-AB sensors suffer from certain shortcomings that have limited their clinical deployment.

Specifically, EA-B sensors, like all complex devices, suffer from inconsistencies in fabrication, wherein different numbers of recognition elements are present on individual sensors, even when manufactured in the same batch. This sensor-to-sensor physical variability means that outputs obtained from different sensors of the same design may vary significantly. Furthermore, when deployed in complex sample environments, such as whole blood, even the best E-AB's are subject to drift, wherein non-specific interactions between the aptamers and complex mixture of molecules in the sample result in variable readings over time. These factors dictate that calibration steps or signal correction measures must be performed in order to interpret sensor outputs. In the case of sensors implanted in vivo, where calibration is not practical or is often impossible, the sources of error described above present a serious obstacle to clinical implementation.

Accordingly, there remains a need in the art for novel electrochemical sensor system and methods of operating such sensors that enable calibration-free measurement. Furthermore, there remains a need in the art for a means of accurately measuring analytes in vivo without being confounded by signal drift. There also remains a need in the art for improving the performance and efficiency of existing sensing platforms.

SUMMARY OF THE INVENTION

Prior art electrochemical sensing methods have relied on measurements of current output (i.e. absolute current values), such as SWV peaks, to determine target concentration, which such measurements are strongly affected by sensor-to-sensor variability and sensor drift. The inventors of the present disclosure have advantageously discovered that certain aspects of the signal output kinetics of electrochemical sensors, specifically, current decay kinetics, are insensitive to sensor-to-sensor variability and sensor drift. Like absolute currents, these current decay kinetic parameters are responsive to target binding in a concentration-dependent manner, but unlike absolute currents, they are stable across sensors of a given class, and are stable over time, providing a means of avoiding the variability observed in absolute currents.

The inventors of the present disclosure have advantageously developed novel methods of operating electrochemical sensors and interpreting sensor outputs, enabling signals generated by different sensors or at different times to be accurately correlated with target concentration in the sample. The methods of the invention enable sensors within a class (e.g., employing the same recognition element) to be effectively calibrated a priori and to be deployed for extended, calibration-free measurement of target species in complex environments, such as whole blood in vivo.

In a first aspect, the scope of the invention encompasses methods of obtaining and interpreting sensor outputs to provide accurate measurements of target analyte concentration. In another aspect, the scope of the invention encompasses sensor systems that may be operated with drift-free or calibration-free measurement. In another aspect, the scope of the invention encompasses electrochemical sensors of a given class, wherein the sensor's outputs is correlated with target concentration by a relationship that is stable across all sensors of the class. In another aspect, the scope of the invention encompasses computer programs, software, and operations which enable the acquisition and interpretation of electrochemical sensor outputs to measure target concentration.

BRIEF DESCRIPTION OF THE DRAWINGS

FIGS. 1A and 1B. FIG. 1A depicts the basic operation of an E-AB sensing platform, wherein an aptamer (102) bound to an electrode substrate (101) is modified with a methylene blue redox reporter (103). In the absence of target, electron flow (104) between the methylene blue and substrate is slow. When target (105) binds to the aptamer, the resulting conformation change alters the proximity of the reporter (103) to the substrate (101), increasing the rate of electron transfer (104). FIG. 1B depicts a representative square wave voltammetry trace for this type of E-AB sensor wherein peak current is higher in the presence than in the absence of target.

FIG. 2A depicts SWV titration curves for a set six of aminoglycoside-detecting sensors using tobramycin as a target. The absolute peak currents generated using SWV depend not only on the concentration of the target molecule, but also on the number of redox-reporter-modified probes on the sensor surface. Due to variations in the active area of the working electrode and the density of the aptamer probes packed onto it, these absolute peak currents can vary significantly from sensor to sensor, leading in turn to large variations in raw (uncalibrated) sensor output. FIG. 2B depicts sensor outputs of FIG. 2A when normalized by performing a calibration step.

FIG. 3 depicts a current transient log-log plot of average current vs. time measured by chronoamperometry of aminoglycoside-binding E-AB sensors in flowing whole blood. The current decay is well described as the sum of two exponential phases. From left to right, a first phase, to the left of the dotted vertical line, is the decay of double layer charging current, wherein the sensors are insensitive to target. To the right of the vertical line, current transients are highly target dependent. In transients obtained in the absence of target, a slower exponential decay of faradaic current is observed. In the presence of target (here tobramycin), the average current lifetime is substantially reduced. The illustrated transients were recorded by stepping the potential from −0.1 V to −0.3 V (all potentials reported versus Ag/AgCl) and sampling the resultant current every 10 µs. The solid lines are multi exponential fits of the experimental data.

FIG. 4A depicts average chronoamperometry-measured current transients for aminoglycoside-binding E-AB sensors (with tobramycin as the target) with decaying current transients with lifetimes that decrease with increasing target concentration. The solid lines represent mono-exponential fits of the two current transients. FIG. 4B depicts the relationship between current lifetime and target concentration in buffer and whole blood, established for a set of aminoglycoside-binding E-AB sensors. The differences in lifetimes between the two sample types are likely due to changes in electrolyte composition and viscosity that affect electron transfer from methylene blue. FIG. 4C depicts tobramycin concentration measured by five sensors of the same class as used to generate the standard curve of FIG. 4B, but which were not used to generate the standard curve. Using these independent sensors to estimate the concentration of tobramycin in flowing whole blood by the curve generated for the sensor class, accurate and precise measurements of tobramycin concentration were obtained over a broad range of concentrations without the need to calibrate individual sensors. Measured concentration values are within 10% of the actual (spiked) concentration of tobramycin over the range from 1 µM to 1 mM when challenged in undiluted whole blood. In FIG. 4B and FIG. 4C the error bars (which are so small as to be difficult to see in FIG. 4B) represent the standard deviation.

FIG. 5A depicts E-AB sensor output in flowing whole blood (here lacking target), where the average peak current recorded from SWV drifts significantly over the course of a few hours (uncorrected signal). Kinetic differential measurements correction techniques applied to the measurements provide a corrected signal. FIG. 4B depicts average current amplitude and average current lifetime for the same sensors deployed in whole blood (lacking target) over time. The amplitude of the chronoamperometric current decays drift quite significantly over the test period. However, in contrast, the current lifetimes are stable across time and do not drift over the course of the test period.

FIG. 6A depicts sensor placement in the jugular vein of a live, anesthetized rat. Sensors were encased in a 22-gauge catheter for structural support, and placed inside the external jugular vein at a depth of 2 cm. An infusion line was implanted in the opposite side to carry out drug infusions. FIG. 6B depicts real-time non-linear regression analysis of the current transients generated by chronoamperometry to extract current lifetimes and convert them to target concentration in real time. The trace is the rolling average of 20 points. The dotted box depicts the timeframe during which tobramycin was infused. FIG. 6C depicts the lifetime vs. time trace (rolling average of 20 points) at 300 ms per time point, wherein the time resolution of this approach is sufficient to monitor not only the injection of the drug but also the subsequent few tens of seconds "mixing" phase associated with the drug homogenizing within the circulatory system. This panel corresponds to the zoomed area marked in dashes from FIG. 6B. FIG. 6D depicts the average concentration vs. time, wherein the unprecedented time resolution enables measurement of the minute-scale distribution phase of the drug with more than 1,000 experimental points, producing in turn ultra-high precision estimates of the associated pharmacokinetic parameters.

DETAILED DESCRIPTION OF THE INVENTION

Figure 2B:
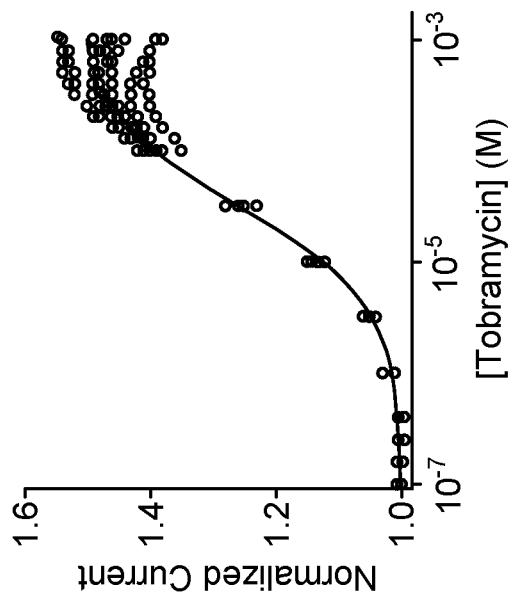
FIGS. 2A and 2B.

Operating Principal. The inventions disclosed herein were derived by extensive study of electrochemical sensor operations and the discovery that certain outputs are insensitive to sensor fabrication variability and signal drift. In standard electrochemical sensor implementation, current flows are altered by target binding and are assessed by voltammetric methods, including cyclic voltammetry, alternating current voltammetry, and square wave voltammetry. These methods measure peak currents, which are related to the fraction of redox-reporter-modified recognition elements that are bound, but are also highly dependent on the total number of recognition elements (e.g., aptamers) present and active on the sensor.

The inventors of the present disclosure have developed an alternative approach for monitoring changes in electron transfer induced by target binding. Rather than measuring voltammetric peak currents, which are indirectly related to binding-dependent electron transfer kinetics, electron transfer kinetics can be measured directly, and, advantageously, the inventors of the present disclosure have discovered that these values are insensitive to the sources of error that affect peak current measurements. The inventors of the present disclosure have determined that the electron transfer kinetics measured via chronoamperometric current decays are largely determined by target binding and, unlike peak currents, are independent of the number of active recognition units on each sensor. Accordingly, the relationship between target concentration and electron transfer kinetics can be determined for a selected sensor configuration and this relationship will be stable and applicable to all like sensors operating under similar conditions. Furthermore, this predictive relationship is also stable for an individual sensor operating for long periods of time.

This novel operating principal of the invention obviates the need to calibrate individual sensors, and provide a means for drift-free operation in challenging environments, such as in vivo. The measurements can also be obtained on extremely fine time scales, enabling resolution of biological processes by electrochemical sensors at time scales of milliseconds.

The various elements of the invention are described next.

Electrochemical Sensors. The various embodiments of the invention are directed to methods of using electrochemical sensors. As used herein, an electrochemical sensor is any sensor that is capable of measuring the concentration of a target species in a sample, wherein binding of the target species to a recognition element of the sensor induces measurable changes in current output by the sensing element, such that the output of the sensor can be used to estimate the concentration of the target in the sample.

EAB Sensors. In a first implementation, the electrochemical sensors utilized in the methods of the invention comprises E-AB sensors. Any E-AB sensor design or configuration known in the art may be used. In an E-AB sensor, the recognition element comprises an aptamer, as known in the art. The aptamer may comprise a DNA aptamer, RNA aptamer, or an aptamer comprising non-natural nucleic acids, as well as hybrids of the foregoing. Variants of the E-AB concept wherein the recognition element is other than a nucleic acid, for example sensors using proteins, chemical species, and other molecules, are also within the scope of the invention.

In an E-AB sensor, one or more selected portions of the working electrode are functionalized with the aptamer. The aptamer may be conjugated to or otherwise associated with the electrode surface by any appropriate chemistry, for example by covalent bonding, chemisorption, or adsorption. Alkane thiol monolayers may be used to conjugate aptamers to the electrode surface, being particularly suitable for gold electrode surfaces.

Each aptamer is functionalized with one or more redox reporters. Binding of the target species causes the aptamer to change its configuration, such that the position of (or the accessibility to the electrode of) the one or more redox reporters is detectably altered. The redox species may comprise any composition of matter that interacts with the electrode such that a change in its accessibility to or proximity to the electrode causes a change in the electron transfer kinetics. Exemplary redox species include methylene blue, ferrocene, viologen, anthraquinone or any other quinones, ethidium bromide, daunomycin, organo-metallic redox labels, for example porphyrin complexes or crown ether cycles or linear ethers, ruthenium, bis-pyridine, tris-pyridine, bis-imidizole, ethylenetetracetic acid-metal complexes, cytochrome c, plastocyanin, and cytochrome c'.

In some implementations, the E-AB sensor is a signal-on type sensor, such that target binding enhances the signal, and in other implementations the E-AB sensor may comprise a signal-off configuration. In one embodiment, the E-AB is a dual-strand sensor, wherein the redox species is present on a separate strand, a portion of which is complementary to or otherwise capable of reversibly binding to a portion of the aptamer. In the presence of the target species, the redox species' strand is liberated from the aptamer, allowing the target species to bind to the aptamer and the redox species to come into contact or proximity to the electrode.

Sensor Components. The electrochemical sensor will comprise one or more working electrodes, to which a plurality of recognition elements are bound (for example, at densities of $0.1 \times 10^{11}$ to $1 \times 10^{13}$ molecules/cm$^2$). The working electrode may comprise any suitable electrode material for electrochemical sensing, including, for example: any metallic surface that forms a bond with thiols or amines; gold; any gold-coated metal, (such as titanium, tungsten, platinum, carbon, aluminum, copper, etc); bare palladium electrodes, carbon electrodes, etc.

The working electrode may be configured in any desired shape or size. For example, paddle-shaped electrodes, rectangular electrodes, wire electrodes, electrode arrays, screen-printed electrodes, and other configurations may be used. For in vivo measurements, a thin wire configuration is advantageous, as the low profile wire may be inserted into veins, arteries, tissue or organs and will not impede blood flow in blood vessels or cause substantial damage in tissues. For example, a wire having a diameter of 1-500 µm, for example, 100 µm, may be used.

The electrochemical sensing systems of the invention further comprise an auxiliary or counter electrode, for example, a platinum auxiliary electrode. The electrochemical sensing element may be used with a reference electrode, for example an Ag/AgCl electrode, or other reference electrode known in the art. The electrochemical sensor of the invention may be configured in a two-electrode or a three-electrode system, appropriately configured for performing chronoamperometric measurements. The electrode-containing cell system may comprise a mixing chamber or other vessel wherein the electrodes are present and are in contact with the sample.

The sensor and electrode system may comprise an assembly for obtaining faradaic current measurements when deployed in the sample or exposed to the sample. The assembly may comprise a housing. For example, for placement in the body of a living organism, the housing may comprise a needle, catheter, or other implantable structure. For ex vivo applications, the housing may comprise a well, microfluidic vessel, or other structure, such as found in a lab-on-chip device.

The electrochemical sensors of the invention will be in functional connection with appropriate components for performing chronoamperometry measurements. The chronoamperometry components may comprise two or more devices in electrical and/or network connection with one another, or may comprise a single integrated device.

A first component for performing chronoamperometry measurements comprises a device or combination of devices that can deliver excitation voltage pulses of a desired magnitude, frequency, and waveform to the sensing element. Chronoamperometry components may include potientiostats or other voltage sources and voltage controllers for imposing voltage steps on the working electrode.

A second component for performing chronoamperometry measurements comprises a device or combination of devices that can acquire time-resolved faradaic current outputs from the sensing element. These components will comprise circuitry for reading sensor outputs and storing such outputs or routing the outputs to other devices, including components as analog-to-digital converters, amplifiers, and storage media. Resolution at very fine time scales will be necessary for measuring the current decay kinetics in most sensor systems, for example, time scales of microseconds to milliseconds.

Other Sensor Types. The scope of the invention is not limited to E-AB sensors. The scope of the invention further encompasses any electrochemical sensor wherein target binding to recognition elements creates measurable changes in electron transfer rates measurable by the sensing element. In one aspect, sensors that employ non-mediated electrochemical sensing may be used, including the use of direct electron transfer and redox equilibrium as a way to generate a signal. These biochemical sensors include, for example, sensors that detect the consumption or generation of species belonging to redox couples. Other sensors may employ a mediated electrochemical analysis, i.e. using a redox species mediator for electron transfer and establishing redox equilibrium. Examples of mediated and non-mediated sensors can be found in Sander et al. 2015, A Review of Nonmediated and Mediated Approaches. *Environ. Sci. Technol.* 49:5862-5878.

Additional sensor types include chemically modified electrodes, immunosensors, oligopeptide-based sensors, and sensors that utilize, organelles (e.g. chloroplasts, mitochondria), animal and vegetable tissues, microorganisms, enzymes, tissue slices, peptides, and antibodies.

Additional sensor types include sensors that measure changes in electron transfer from solution-phase redox reporters, for example, ferrocyanate/ferricyanate redox coupled with a 17mer peptide that specifically recognizes cyclic AMP, as described in Katayama et al. 2000, The Design of Cyclic AMP-Recognizing Oligopeptides and Evaluation of Its Capability for Cyclic AMP Recognition Using an Electrochemical System. Anal Chem. 2000; 72 (19): 4671-4.

Another sensor architecture that may be used is a polymeric sensor, such as a sensors using cationic polythiophene bearing a ferrocene substituent as a mediator in an aptamer system as described in Le Floch, 2006, Label-Free Electrochemical Detection of Protein Based on a Ferrocene-Bearing Cationic Polythiophene and Aptamer. Anal Chem. 2006; 78 (13): 4727-31. doi: 10.1021/ac0521955.

Another sensor type that may be used is a sensor based on electron transfer changes due to target binding-induced displacement of ligands, for example, hexamethylphosphoramide with samarium (II) iodide as described in Prasad, 2004, The Role of Ligand Displacement in Sm(II)-HMPA-Based Reductions. J Am Chem Soc. 2004; 126 (22): 6891-4.

Another exemplary sensor type is based on changes in a redox reporter's reorganizational energy, for example, ferrocenoyl-peptides as described in Plumb, 2003, Interaction of a Ferrocenoyl-Modified Peptide with Papain: Toward Protein-Sensitive Electrochemical Probes. Bioconj Chem. 2003; 14 (3): 601-6. doi: 10.1021/bc0256446; or trinuclear ruthenium clusters, for example, as described in Feld 2012, Trinuclear Ruthenium Clusters as Bivalent Electrochemical Probes for Ligand-Receptor Binding Interactions. Langmuir. 2012; 28 (1): 939-49. doi: 10.1021/la202882k.

Another sensor type that may be used is a sensor based on sterically induced changes in the efficiency with which a scaffold-attached redox reporter approaches an underlying electrode surface, for example, duplex DNA, quadruplex DNA, and DNA nanoswitches as described in Ge 2010, A Robust Electronic Switch Made of Immobilized Duplex/Quadruplex DNA. Angew Chem Int Ed. 2010; 49 (51): 9965-7. doi: 10.1002/anie.201004946, or DNA-containing a small molecule recognition element as described in Cash 2009, An Electrochemical Sensor for the Detection of Protein-Small Molecule Interactions Directly in Serum and Other Complex Matrices. J Am Chem Soc. 2009; 131 (20): 6955-7. doi: 10.1021/ja9011595.

Sensor Class. The various methods of the invention are based on the discovery that certain sensor outputs, i.e. current decay kinetics, are stable among sensors of a given type. A class, as used herein, refers to a plurality of sensors having one or more shared characteristics. The sensor characteristics may comprise various factors, including: the configuration and materials of the electrodes, the type of sample to be analyzed, the type of recognition element, the type of redox reporter(s) and placement thereof, the packing density of the recognition elements on the working electrode, the electrode functionalization chemistry, and other sensor parameters that affect sensor output. Another class parameter may be the sensor's manufacturing lot, wherein sensors in a class are those fabricated in the same allotment.

In one embodiment, a class of sensors comprises a plurality of sensors having substantially identical sensor architecture, identical recognition elements and redox reporter elements, identical chemistries for attachment of the recognition elements to the working electrode, identical manufacturing methods, and similar recognition element packing densities (e.g., packing densities that vary by 1-20% among sensors within the batch in terms of moles of probe per square centimeter).

Target Species. The sensors employed in the methods of the invention are directed to the detection of a target species. The target species may comprise any inorganic or organic molecule, for example: a small molecule drug, a metabolite, a hormone, a peptide, a protein, a carbohydrate, a nucleic acid, a lipid, a hormone, metabolite, growth factor, neurotransmitter, or a nutrient. The target may comprise a pollutant or contaminant. The target may comprise a toxin. The target may comprise a pathogen-induced or pathogen-derived factor, or a virus or cell. In some embodiments, the target species comprises a drug having significant side effects, such as a chemotherapeutic drug, or a drug having a narrow therapeutic index, wherein accurate measurement of blood level is critical to ensure safe dosing or minimal side effects.

Operating Conditions. Sensors are utilized under selected operating conditions, which encompass various aspects of the detection process. Operating conditions may encompass any combination of factors that affect the operation and output of the sensor.

In a first aspect, the operating conditions encompass the sample type to be analyzed. The target species of the invention are assessed in a sample. The sample will comprise a liquid. The sample may comprise whole blood, serum, saliva, urine, sweat, interstitial fluid, spinal fluid, cerebral fluid, tissue exudates, macerated tissue samples, cell solutions, intracellular compartments, water, wash water, wastewater, groundwater, food, beverages, or other biological and environmental samples. In some embodiments, the sample is derived from a subject, for example a human patient or a non-human animal such as a veterinary subject or test animal. In one embodiment, the sample comprises flowing whole blood, i.e., blood sampled by a sensing system comprising a sensor implanted in the living body (e.g., in the circulatory system) of a subject. In an alternative embodiment, the method is used to measure target species in a gas, wherein the gas has equilibrated with the liquid sample.

In one embodiment, the sample is processed prior to measurement. Examples of processing include filtering, dilution, buffering, centrifugation, and the application of other materials or processes to the sample prior to analysis. In some embodiments, the sample is not processed prior to performing measurements, for example, the sample being undiluted, unfiltered, or unconcentrated.

In a second aspect, the operating conditions encompass the assay conditions. The general assay conditions will refer to reaction conditions for the assay, such as sample volume, temperature, pH, etc.

In a third aspect, the operating conditions may be defined by operational parameters used to obtain sensor measurements. For example, shape and frequency of the applied voltage waveform, voltage step values, and sampling intervals are some of the variables that constitute operational parameters.

Measurement of Target Concentration by Current Decays. In a first aspect, the invention encompasses a general method of measuring the concentration of a target species in a sample by the use of an electrochemical sensor. The method encompasses the following general steps:

(A) a mathematical relationship between a selected measure of current decay and target concentration is determined for a selected class of electrochemical sensors operating under a selected set of operating conditions;

(B) an electrochemical sensor of the selected class is deployed in a sample of unknown target concentration, under the selected operating conditions, and a value of the selected measure of current decay is acquired; and (C) applying the relationship between current decay and concentration established in step (A), the current decay value observed in step (B) is used to determine the concentration of the target species in the sample.

For example, in one embodiment, the invention encompasses a method of measuring the concentration of a target species in a sample by the use of an electrochemical sensor, the method comprising the steps of:

deploying an electrochemical sensor such that it is exposed to a sample, wherein the output of the electrochemical sensor is a faradaic current that varies in a concentration-dependent manner to the concentration of a target species in the sample;

applying one or more excitation pulses to the electrochemical sensor, wherein a time-dependent faradaic current output is generated by each pulse;

acquiring time-resolved faradaic current data following each of the one or more excitation pulses;

by the acquired time-resolved faradaic current data, calculating the value of a selected measure of current decay;

by the calculated value of a measure of current decay, calculating the concentration of the target species by application of a mathematical relationship between selected measure of current decay and the concentration of the target species in the sample.

Measure of Current Decay. The inventors of the present disclosure have advantageously determined that the decay rate of current transients generated in response to an excitation stimulus are related to the concentration of the target species and are stable across sensors of the same class. The methods of the invention thus rely on the measurement of current decay, the relationship between current decay rate and target concentration, and the remarkable stability of this relationship among like sensors and over time. The lifetime of chronoamperometric decays depend only on the relative populations of the bound and unbound recognition elements (e.g. aptamers), not the absolute numbers of bound and unbound recognition elements, and thus provides a way to measure target concentration that is independent of factors that may vary significantly between individual sensors of the same class.

For example, in the case of an electrochemical sensor comprising an electrode substrate functionalized with a plurality of recognition elements, wherein each recognition element is functionalized with one or more redox reporters, electrical excitation of the redox reporters will induce a temporary flow of current between the redox reporters and an electrode substrate (or between the electrode substrate and the redox reporters, depending on the configuration of the system). Upon stepping the voltage of a working electrode, such as the substrate of an E-AB sensor, the working electrode becomes either a stronger reducing agent (in the case of stepping to a more negative potential) or a stronger oxidizing agent (in the case of stepping to a more positive potential). Within appropriate ranges (e.g., near or above the redox potential of the redox reporter), this step in voltage will induce a faradaic current flow between redox reporters of the sensor's recognition elements and the electrode substrate. As current flows, the pool of electrons mobilized by the excitation becomes depleted, and the current will decay exponentially (or multi-exponentially) at rates and amplitudes dependent upon the binding status of the recognition elements of the sensor, wherein target binding induces faster or slower transfer of current, for example, by changing the proximity of the redox reporter to the working electrode. Accordingly, the ratio of target-bound recognition elements to recognition elements not bound by the target, which ratio is proportional to the concentration of the target species in the sample, will determine the observed current decay rates and amplitudes for the sensor as a whole.

As used herein, "current" will refer to the flow of electrons measured by a sensor that has been deployed in a sample. For example, current may comprise flow of electrons from redox reporters to an electrode, or may comprise the flow of electrons from an electrode to redox reporters. "Current decay," as used herein, means the behavior of current transients measured by the sensor over time in response to the application of an excitation stimulus to the sensor or sample.

The measurement of current decay may be achieved using chronoamperometric methods, as known in the art. Decay parameters may be measured by applying an excitation to the sensor and/or sample and measuring the response of current over a period of time following the excitation. The measurement of decay parameters thus requires a sensor or sample environment in connection with components that (1) deliver excitation pulses of a desired voltage, frequency, and waveform; and (2) measure the current response over time scales corresponding to the duration of the current transients.

The excitation pulse may be stimulus of any kind that induces a current transient, for example, a stepping of the sensor electrode's potential to values where redox reporters will be substantially (e.g., fully) oxidized or reduced. Appropriate excitation waveforms may be selected, as known in the art. For example, voltage steps in the range of +/−0.1 V to 0.5 V may be utilized, at repetition rates of 1 to 10,000 Hz, for example 5 Hz, 10 Hz, 20 Hz, 50 Hz, 100 Hz, and intermediate values between 1 and 10,000 Hz.

Acquisition of time-resolved current measurements at time scales of microseconds to milliseconds will typically be required. Typical current transients have a duration in the range of 10-100 ms, and may be resolved by sampling at shorter time intervals, for example, every 1 µs, 2 µs, 3 µs, 5 µs, or 10 µs.

Once time-resolved current data has been acquired, these data may then be analyzed to derive any number of mathematical parameters that describe the kinetics of the current decay. The selected measure of decay may be any parameter of the current transient which varies in a concentration-dependent manner to the concentration of the target species in the sample. The selected measure of current decay can be assessed as any measure of decay kinetics, for example, a rate constant, lifetime, half-life, or any other quantification of current decay. For example, in one embodiment, as described below, the measure of decay is derived by fitting the entire decay curve to a function and employing the lifetime (inverse rate constant) or half-life for that decay curve. In another embodiment, as described below, the decay is derived by fitting the time-resolved data to a function that derives the sum of two or more exponentials and employing the relative amplitudes, or like measures, of the exponential components.

A selected mathematical analysis is applied to the acquired, time-resolved current data to derive the selected measure of decay. Any regression analysis may be applied to derive the selected measure of current decay, to resolve the coincident electron transfer of bound and unbound recognition elements. In one embodiment, the measure of current decay is derived using a monoexponential fit to the sensor current trace. In one embodiment, the measure of current decay is derived using a multiexponential fit. In one embodiment, the measure of current decay is derived using a biexponential fit. In one embodiment, the measure of current decay is derived using a triexponential fit. A current decay value may be assessed by a single data point, or by the averaging of multiple data points. For example, a sampled decay value may comprise an average value observed over a selected number of excitation-decay cycles ranging between 1-100 cycles, for example, 5, 10, 20, 50, 75, or 100 cycles or intermediate values thereof.

In some sensor systems, the kinetics of interconversion between the bound and unbound states of the recognition element are faster than the electron transfer events measured by the sensor. Thus, the observed current transients reflect a population-weighted average of the bound and unbound states. This may be analyzed by approximating the current decay lifetime using a mono-exponential fit, for example as in FIG. 4A. The lifetime of this "best fit" mono-exponential is monotonically related to the concentration of the target. In other words, current decay traces which are best described as the sum of two exponential processes (unbound decay and bound decay) can be fit with a monoexponential curve, the parameters of which (e.g., decay constant, half-life, etc.) provide a means of determining target concentration.

In one embodiment, the selected measure of decay is derived by fitting the time-resolved current data to a function that derives the sum of two exponents and using the relative amplitude of the exponential components as a measure of target binding. For example, as the observed current decay is a combination of bound and unbound decays, a biexponential fit may be used to describe the decay curve, with a more rapid phase representing target-bound decays and a slower phase representing unbound decay. The relative amplitude of either decay, i.e., its amplitude relative to the total amplitude of the two phases together or the ratio of the amplitudes of the two phases, may be utilized as a measure of the proportion of target-bound recognition elements. In alternative implementations, the decays may be described by three or more exponentials, e.g., a triexponential fit, etc.

For example, exemplary methods of utilizing exponential fits are described in Kamman et al., C., Multi-exponential relaxation analysis with MR imaging and NMR spectroscopy using fat-water systems, In Magnetic Resonance Imaging, Volume 5, Issue 5, 1987, Pages 381-392.

For example, in one implementation, chronoamperometric current decays from the sensors are plotted in log-i (current)-log-t(time) plots, and non-linear regression analysis is performed using the following equations:

For mono-exponential systems, by Equation 1:

$$i = i0_1 * \exp\left(\frac{-t}{\tau 1}\right) + C \quad \text{(Equation 1)}$$

For bi-exponential systems, by Equation 2:

$$i = i0_1 * \exp\left(\frac{-t}{\tau 1}\right) + i0_2 * \exp\left(\frac{-t}{\tau 2}\right) + C \quad \text{(Equation 2)}$$

For tri-exponential systems, by Equation 3:

$$i = i0_1 * \exp\left(\frac{-t}{\tau 1}\right) + i0_2 * \exp\left(\frac{-t}{\tau 2}\right) + i0_3 * \exp\left(\frac{-t}{\tau 3}\right) + C \quad \text{(Equation 3)}$$

wherein, for Equations 1-3, t is time following the excitation, $\tau$ is the time constant, i is current, and C is constant background current, if any.

The relative amplitudes are calculated as the ratio of one selected amplitude over the sum of all the amplitudes. For example, for a biexponential fit:

$$\text{Relative Amplitude } 1 = \frac{i0_1}{(i0_1 + i0_2)}; \text{and} \quad \text{Equation 4}$$

$$\text{Relative Amplitude } 2 = \frac{i0_2}{(i0_1 + i0_2)} \quad \text{Equation 5}$$

Figure 2A:
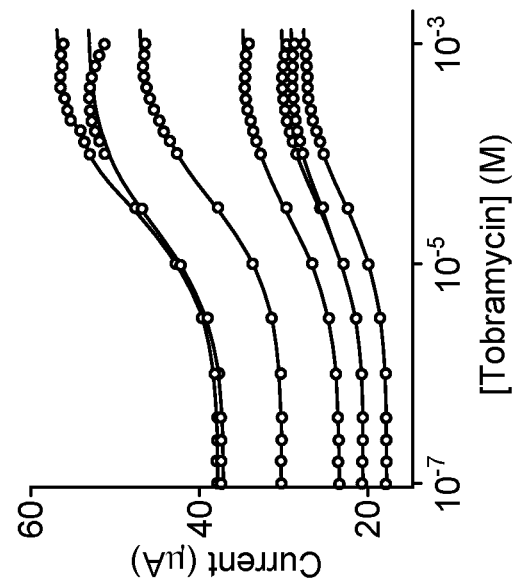
Figure 3:
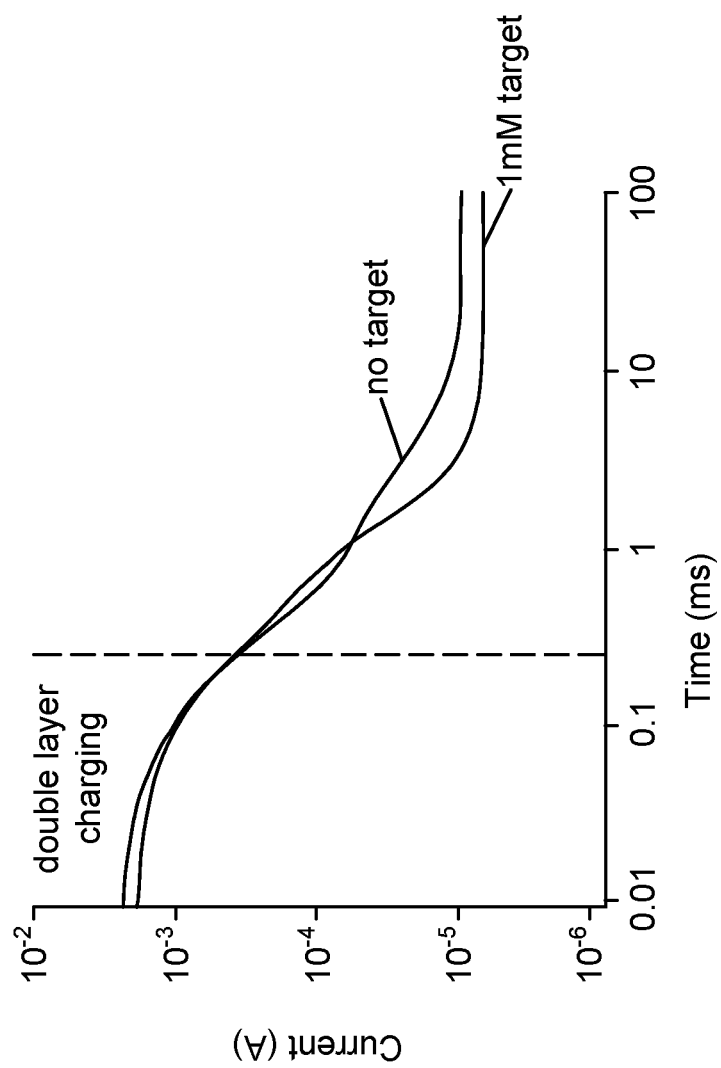
FIG. 3.

FIG. 3 provides an illustration of current decay dynamics for an electrochemical sensor. In this example, pulsed voltage is applied to an E-AB sensor comprising methylene blue redox reporters and the current is measured following the pulse. Two curves are presented, a first depicting current dynamics for a sample comprising no target, and a second depicting current dynamics for a sample comprising a saturating concentration of target (i.e., under which all recognition elements aptamers of the sensor are bound by target). Upon application of a step in voltage at a sufficiently negative potential, the complete reduction of all methylene blue reporters is achieved. The flow of these electrons is measured over time following the end of the pulse. In a first phase, typically about 0.1 ms after application of the pulse in aqueous solutions, the decay is rapid. This phase is attributed to charging of the electrical double layer formed on the electrode surface at this potential bias (i.e., the migration of aqueous ions that has time-scales of microseconds). The double layer charging decay is largely insensitive to target concentration in the sample and is generally not useful for predicting target concentration. Following this phase, a second phase is observed, wherein the decay kinetics are strongly related to target binding, corresponding to the faradaic reduction of the reporter, e.g., methylene blue to leucomethylene blue. In FIG. 2, for the target-saturated recognition elements, a fast exponential decay in current is observed, with a lifetime of 100±30 μs. For the recognition elements in a target-free sample, a slower decay is observed with a lifetime of 6.5±0.5 ms. The ~ 5 fold decrease in lifetime (when comparing saturated samples to samples devoid of target) corresponds to a change in the proximity of the redox reporter to the electrode surface and reflects a population of target-bound aptamers that transfers electrons more rapidly than the target-free aptamer.

Class Calibration. In one aspect, the scope of the invention is directed to a method of calibrating a class of sensors, by means of a representative subset of sensors in the class. The purpose of the calibration step is to generate a standard curve for the interpretation of sensor outputs for all sensors in the class. Accordingly, the calibration of sensors of a given class is performed using representative sensors of the same design, assaying representative samples, under operating conditions similar to and/or representative of those in which the sensors will be deployed. Once such calibration has been performed using the representative subset, other sensors from the class may be used to perform calibration-free measurement of the target species under similar operating conditions.

Class calibration is achieved by establishing a "decay-concentration relationship" for the selected sensor type in representative samples under the selected operating conditions. The decay-concentration relationship is a predictive relationship between target concentration in a sample and the observed current decay value resulting from a step in voltage at the working electrode. The decay-concentration relationship may be calculated using any appropriate regression analysis. As signal output is a combined sum of bound and unbound decays, models which estimate a monotonic function based on the sum of two exponential decay curves will be well suited to the calculation step. For example, if current lifetime is the selected measure of current decay, a relationship between current lifetime and concentration is determined. In another embodiment, calibration data is fitted to extract multiple exponential processes, and relative amplitudes calculated for each exponential phase serve as the measure of decay, such that a relationship between relative amplitude and concentration is established.

The calibration measurements used to establish the relationship in Step (A) are performed using a set of standards of various and known target concentrations. Measurements should be made across a range of target concentrations within the dynamic range of the sensor, i.e., from zero target to saturating target levels, for example by the use of spiked samples. Any number of data points may be generated, for example 2-1,000 data points may be sampled to generate the calibration data. For example, 25-100, e.g., 50-75 data points may be used in the calibration.

The class calibration process will employ a representative set of sensors. The representative set will comprise a sufficient number of sensors to provide a calibration curve that is accurately predictive for other sensors in the class. The number of sensors in the representative set may be established, for example, by methods known in the art for determining a sample mean based on sub-sample values. A representative set may comprise, for example 1, 3, 5, 10, 20, 50, 100, or more sensors, and values intermediate thereto.

FIG. 3B illustrates a calibration curve of the invention. For five E-AB aminoglycoside-detecting sensors, current lifetime was assessed across a range of concentrations, in both whole blood and buffer. A "best fit" mono-exponential was monotonically related to the concentration of the target by a non-linear regression of lifetime versus concentration to a Langmuir isotherm. These results illustrate the effects of different operating conditions on sensor output, wherein the blood and buffer calibration curves are different.

Sensors of a given class, operated under similar operating conditions, will have sufficiently similar decay outputs to enable the prediction of target using a standard curve generated for all sensors of that class. Sensors of the same class may have decay outputs that, when exposed to a like sample comprising a given target concentration, will have values of a selected current decay measure that diverge by less than 20%, less than 15%, less than 10%, less than 5%, or less than 1% depending on the stringency of manufacturing, signal-to-noise inherent in the system, and other variables.

In one embodiment, the scope of the invention encompasses a class-calibrated sensor. A class-calibrated sensor means a sensor of a selected class, e.g., having a selected recognition element, selected redox reporter, selected electrode attachment chemistry, selected electrode configuration, and other parameters that define sensor performance, wherein a decay-concentration relationship between a selected measure of current decay and the concentration of a selected target is known for sensors of the class. In one embodiment, the class calibrated sensor is an aptamer-based electrochemical sensor.

Calibration-Free Measurement. In one aspect, the scope of the invention comprises a method of calibration free-measurement of target species concentration. Calibration-free operation, as used herein, means the operation of an electrochemical sensor of a selected class wherein the sensor output (for example, current decay lifetime or relative amplitudes) is directly converted to a target concentration value by use of a calibration curve specific for the selected class. In calibration-free operation, the sensor is not necessarily calibrated prior to, during or after measurement.

Figure 5B:
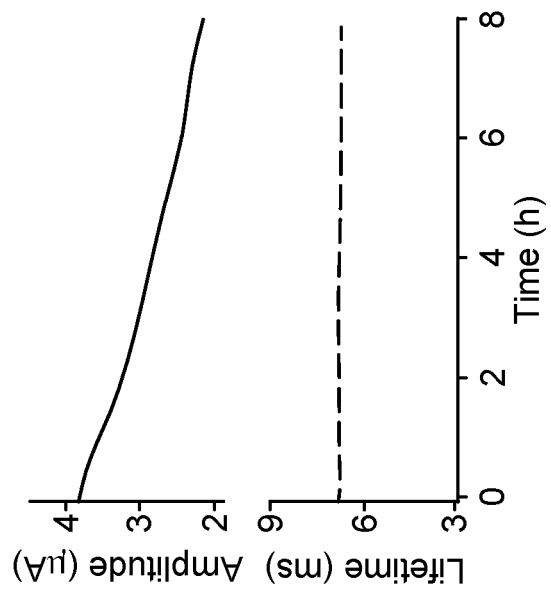
FIGS. 5A and 5B.
Figure 5A:
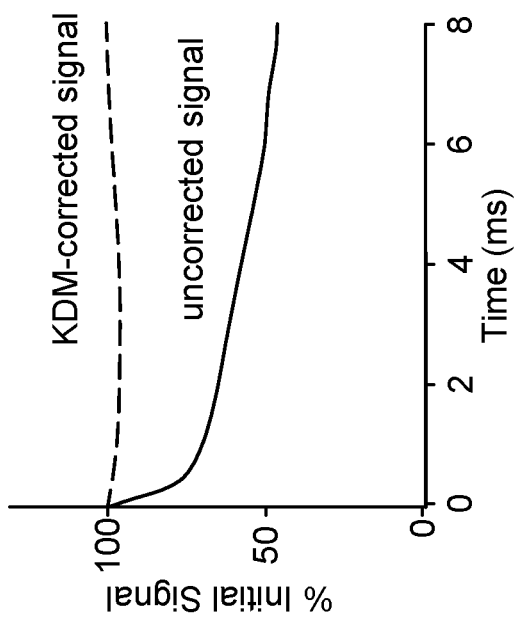

Drift-Free Operation. In one aspect, the scope of the invention encompasses the drift-free operation of an electrochemical sensor, wherein the sensor is operated for an extended period of time, e.g. hours, days, months, or longer. As depicted in FIG. 5A, E-AB sensors deployed directly in flowing whole blood will have outputs that drift considerably when sensor output is measured as an amplitude by square wave voltammetry. This severe baseline drift is eliminated current lifetime is measured instead, as in FIG. 5B, wherein current lifetimes are stable for a period of 8 hours, while absolute sensor output drifts considerably during the test period.

Subsecond Temporal Resolution. The methods of the invention enable calibration-free, sub-second-resolved measurement of molecules directly in vivo. As set forth in the Examples, real-time resolution of target concentration in the blood or other body compartment is enabled by the methods of the invention, for example with time scales of 100-500 ms. The unprecedented temporal resolution of this approach enables the measurement of rapidly fluctuating target dynamics during physiological events, such as drug uptake and distribution, hormone and neurotransmitter release, and other physiological events taking place over short time scales. The fine time-scale resolutions enabled by chrono-amperometry make the methods of the invention especially well suited to pharmacokinetic analysis. In one embodiment, the invention encompasses the real-time calculation of pharmacokinetic parameters by the calibration-free measurement of drugs, metabolites, excretion products, or other species involved in drug metabolism.

Sensor Deployment and Operation. The inherent stability of electron transfer kinetics across sensors of a class operated under similar operating conditions enables the use of electrochemical sensors in various contexts. In various implementations, the methods of the invention enable sensors to make accurate measurements when deployed in contexts where calibration is impossible, burdensome, or expensive. The calibration-free and drift-free methods of the invention are especially amenable to in vivo measurements. For example, the sensing element or housing of a sensing system may be inserted, implanted, or otherwise placed within the body of a living organism. The sensor element of a sensing system may be implanted in the circulatory system, subcutaneously, intraperitoneally, within an organ, or in other body compartments, wherein the sensing element is exposed to in vivo fluids, e.g., interstitial fluid, blood, for example, flowing whole blood. The implanted sensing system of the invention may comprise an implanted sensing element in connection with components external to the body (e.g. by leads, wires, or wireless communication means) wherein the external components perform pulse generation, data acquisition or processing. Alternatively, the one or more ancillary components to the sensing element, or even the entire sensing system of the invention, may be implanted in the body, with communication (by, for example, leads, wires, or wireless communication devices) to external devices for data collection.

In one embodiment, methods of the invention are performed in a feedback controlled dosing system, as known in the art, wherein a drug is administered to maintain blood concentrations within a therapeutic index or safety index. For example, in such methods and systems, the methods of the invention are applied using an electrochemical sensing element implanted in a subject to measure the concentration of a target species, wherein the target species is a drug, metabolite of a drug, or biomarker indicating that the drug should be administered. When the detected levels of the target species indicate that the subject is in need of administration of a drug or other agent, an implanted pump or other agent delivery means administers the drug or agent metered at a dosage to maintain the concentration of drug or agent within a desired range.

In other contexts, the sensors of the invention are utilized for long-term and/or continuous monitoring of environmental or industrial sites, for example, in rivers, seas, water treatment plants, industrial facilities, food processing facilities, etc.

The sensors of the invention may also be used in ex-vivo diagnostic applications. In one embodiment, the method of the invention comprises the steps of withdrawing a sample from a living organism, and measuring the concentration of the target species in the sample by calibration-free measurement. In one embodiment, the sensors of the invention are employed in point-of-care testing systems. For example, in one embodiment, the sample is a blood sample, for example, a self-withdrawn pin-prick or finger-prick blood sample, or a urine, sweat, or saliva sample. In such embodiments, the electrochemical sensor may be deployed in a housing such as a well, slide, lab-on-chip, microfluidic chamber, or other device.

Chronoamperometry with Calibration. The scope of the invention is not limited to calibration-free chronoamperometry. In one implementation, the accuracy of concentration measurements attained by electrochemical sensors performing chronoamperometry is enhanced by the performance of one or more calibration steps, i.e, wherein a deployed sensor is exposed to one or more samples of known target concentration in order to check for deviation between observed and expected concentration values and to correct for any such deviations. This embodiment still entrains the improved time resolution chronoamperometry affords relative to established electrochemical methods for interrogating sensors in this class.

In another embodiment, the decay-concentration relationship for a deployed sensor is established by calibration. The deployed sensor may be exposed to one more samples of known target concentration in order to establish the decay-concentration relationship for the sensor under its current operating conditions.

Computer Processes and Programs. The scope of the invention encompasses various embodiments comprising software, computer programs, and programmed devices. In one embodiment, the scope of the invention encompasses non-transitory computer-readable recording media having stored thereon data and/or an encoding program that causes a computer to execute series of operations. The computer may comprise any general purpose computer, processor, embedded processor, mobile device, or other computing device. The computer may encompass hardware elements comprising input devices such as keyboards, mouse, touch-screen and other inputs. The computer may encompass hardware elements for the output, storage, or display of data, including graphical user interfaces, displays, and storage devices.

In one embodiment, the invention comprises a non-transitory computer-readable recording media having stored thereon data and/or an encoding program that causes a computer to execute series of operations, wherein the data and/or series of operations causes the operation of an electrochemical sensing system to effect the methods of the invention. In various embodiments, the non-transitory computer-readable recording media may effect operations such as: controlling a potentiostat or equivalent device to deliver a series of stepped voltage pulses to a deployed electrochemical sensor; controlling a data collection device to record sensor current outputs following the delivery of voltage pulses; controlling a processor to perform calculations that derive one or more selected measures of current decay from sensor output data; storing a calibration curve that relates a selected measure of current decay to target concentration; controlling a processor to calculate target concentration based on sensor outputs and a stored calibration curve; storing instructions for the performance of the methods of the invention; and other operations of the invention.

In one embodiment, the scope of the invention encompasses a device programmed to perform the operations of the invention, for example, a device comprising or in connection with (e.g. network connection) the aforementioned non-transitory computer readable medium.

Kits and Systems. The scope of the invention extends to collections of components configured to perform the analyte concentration measurements of the invention. In various embodiments, the scope of the invention encompasses collections comprising two or more items for the performance of the methods of the invention, the two more components being selected from the group consisting of: electrochemical sensors of a class wherein the relationship between a measure of decay acquired by the sensor under selected operating conditions and target concentration is known; sensor housings for deployment of the sensors to a selected sample type; potentiostat and controllers thereof which may deliver electrical signals to generate current transients; data acquisition and computer readable storage media and/or processing means for calculating a selected measure of current decay from sensor current data; computer readable storage media and/or processing means for calculating target concentration from current decay data; and instructions for performing the methods of the invention.

EXEMPLARY EMBODIMENTS

In one embodiment, the invention is a method of measuring the concentration of a target species in a sample by the use of an electrochemical sensor, the method comprising the steps of:
  deploying an electrochemical sensor such that it is exposed to a sample, wherein the output of the electrochemical sensor is a faradaic current that varies in a concentration-dependent manner to the concentration of a target species in the sample;
  applying one or more excitation pulses to the electrochemical sensor, wherein a faradaic current output is generated by each pulse;
  acquiring time-resolved faradaic current data following each of the one or more excitation pulses;

by the acquired time-resolved faradaic current data, calculating the value of a selected measure of current decay;

by the calculated value of a measure of current decay, calculating the concentration of the target species by application of a mathematical relationship between selected measure of current decay and the concentration of the target species in the sample.

In one embodiment, the electrochemical sensor comprises an electrode functionalized with a plurality of recognition elements that undergoes a conformational change upon target binding, wherein each recognition element is functionalized with one or more redox reporters. In one embodiment, the recognition element comprises an aptamer.

In one embodiment, the sample is selected from the group consisting of whole blood, serum, saliva, urine, sweat, interstitial fluid, spinal fluid, cerebral fluid, tissue exudates, macerated tissue samples, cell solutions, intracellular compartments, water, wash water, wastewater, groundwater, food, and beverages. In one embodiment, the sample is not processed prior to measurement.

In one embodiment, the target species is selected from the group consisting of a small molecule drug, a metabolite, a hormone, a peptide, a protein, a carbohydrate, a nucleic acid, a lipid, a hormone, a metabolite, a growth factor, a neurotransmitter, a nutrient, and a pollutant, a pathogen-induced or pathogen-derived factor, a pathogen, or a cell.

In one embodiment the selected measure of target decay is selected from a decay constant, an average lifetime, a half-life, and a relative amplitude. In one embodiment, the selected measure of current decay is derived from an exponential fit of the time-resolved current data. In one embodiment, the selected measure of current decay is derived from a monoexponential fit of the time-resolved current data. In one embodiment, the selected measure of current decay is derived from a biexponential fit of the time-resolved current data.

In one embodiment, the mathematical relationship between the selected measure of current decay and target concentration has been derived for sensors of the same class as the deployed electrochemical sensor.

In one embodiment no calibration step is performed prior to or after the measurement. In one embodiment, repeated measurements are obtained over an extended period of time.

In one embodiment, the electrochemical sensor is deployed in vivo. In one embodiment, the electrochemical sensor is deployed in a human subject. In one embodiment, the electrochemical sensor is deployed in a non-human animal. In one embodiment, the electrochemical sensor is deployed ex vivo. In one embodiment, the ex vivo deployment is in a point-of-care system.

In one embodiment, the electrochemical sensor is configured such that when it is deployed in a sample, the output of the sensor is a faradaic current which varies in a concentration dependent manner to the concentration of a target species in a sample; and wherein a stable mathematical relationship relating a measure of faradaic current decay and target concentration is known for sensors of a class to which the electrochemical sensor belongs.

In one embodiment, the electrochemical sensor comprises an electrode functionalized with a plurality of recognition elements which undergo a conformational change upon target binding and wherein each recognition element is functionalized with one or more redox reporters. In one embodiment, the sensors of the class comprise sensors having the same recognition element type, same redox reporter type, and same attachment chemistry for conjugation to the electrode. In one embodiment, the recognition element comprises an aptamer.

In one embodiment, invention is a sensing system comprising an electrochemical sensor, wherein the electrochemical sensor is configured such that when it is deployed in a sample, the output of the sensor is a faradaic current which varies in a concentration dependent manner to the concentration of a target species in a sample:

hardware components comprising devices for the application of excitation pulses to the electrochemical sensor and the acquisition of time-resolved faradaic current decay from the electrochemical sensor following the application of each pulse; and non-transitory computer-readable medium having stored thereon data and a computer program which enable performance of the methods described herein by the electrochemical sensor and hardware components. In one embodiment of the system, the electrochemical sensor comprises an electrode functionalized with a plurality of recognition elements which undergo a conformational change upon target binding and wherein each recognition element is functionalized with one or more redox reporters. In one embodiment, the recognition element comprises an aptamer. In one embodiment, the electrochemical sensing system is programmed to perform chronoamperometric current decay analyses to derive the concentration of target species in the sample, by the methods disclosed herein. In one embodiment, the sensor element of the sensing system is implanted in the body of an animal and is in wireless or wired communication with ex vivo hardware components. In one embodiment, one or more ancillary hardware elements for delivery of voltage pulses, collection of time-resolved current data, and calculation of target concentration is implanted with the sensor. In one embodiment, the sensor and the ancillary elements, including elements for the delivery of voltage pulses and elements for the collection and analysis of time resolved current data, in addition to a power supply (e.g., battery) are implanted in the body of an animal. In one embodiment, the system further comprises a drug delivery means for administering a pharmaceutical agent to the animal in response to threshold levels of the target species being detected by the methods of the invention, or a means for issuing an alert that a pharmaceutical administration is necessary. In one embodiment, the drug delivery means is a pump. In one embodiment, the means for issuing an alert that a pharmaceutical administration is necessary comprises a wearable or mobile device in wired or wireless connection with implanted sensor system components.

In one embodiment, the invention comprises a non-transitory storage medium having thereon computer readable instructions for operating a chronoamperometric electrochemical sensing system to perform chronoamperometric current decay analyses to derive the concentration of a target species in a sample, by the systems and methods disclosed herein.

EXAMPLES

Example 1. Real-time, sub-second-resolved measurement of specific molecules directly in the living body using chronoamperometrically interrogated E-AB sensors.

Electrochemical, aptamer-based sensors provide a modular approach to the continuous, real-time measurement of specific molecular targets irrespective of their chemical reactivity. The platform, which consists of an aptamer "probe" modified with a redox-active "reporter" and attached to an interrogating electrode (FIG. 1A), signals via a binding-induced conformational change that alters electron transfer from the reporter, leading in turn to an easily measurable electrochemical output (FIG. 1B). Because their signaling mechanism mimics the conformation-linked signal transduction employed by naturally occurring receptors in the body, E-AB sensors are particularly insensitive to non-specific binding and easily support continuous, extended measurements directly in flowing, undiluted blood serum. And while E-AB sensors often exhibit significant drift when challenged in undiluted whole blood, the inventors of the present disclosures have recently shown that, when combined with protective membranes, improved surface passivation chemistries and/or active drift correction mechanisms, E-AB sensors support the continuous, real-time measurement of specific molecules in whole blood and even in situ in the living body over the course of hours.

E-AB signaling is driven by binding-induced changes in the electron transfer kinetics of the aptamer-bound redox reporter. Previously cyclic current, alternating current, or square wave voltammetry has been used to "read out" this change by observation of peak currents. The most commonly employed of these, square wave voltammetry (SWV) achieves this conversion by subjecting the sensor to a series of potential pulses and sampling the resultant faradaic currents after a delay defined by the square wave frequency. The magnitude of the observed current is thus dependent on the electron transfer rate (which defines how much the current has decayed by the time it is measured), which, in turn, depends quantitatively on the concentration of the target. Specifically, when an E-AB sensor is interrogated by SWV the resultant peak current rises or falls monotonically (depending on the square-wave frequency) with rising target concentration (FIG. 1B). The relative magnitude of this binding-induced change (i.e., the signal gain) is dependent on the aptamer employed in the sensor and can be maximized by optimizing the square wave frequency and amplitude.

Although SWV has proven a particularly convenient and reliable means of converting binding-induced changes in electron transfer kinetics into an easily measurable output, the approach is not without limitations. First, the peak currents (measured in amperes) produced by SWV are dependent not only on the presence or absence of target but also on the number of redox-reporter-modified aptamers on the sensor's surface, which can fluctuate significantly from device-to-device due to variations in fabrication (FIG. 2A). Previously, this this variation was addressed by calibrating each device in a reference sample of known (typically zero) target concentration prior to use, which, while effective (FIG. 2B), increases complexity. Second, while SWV-interrogated E-AB sensors are selective enough to deploy directly in undiluted blood serum, they exhibit significant drift when deployed either in vitro or in vivo in whole blood a problem that, has previously been overcome using a variety of drift correction and drift-avoidance mechanisms. Finally, because of the time required to scan the necessary several hundred millivolt potential window of SWV, its time-resolution is limited to several seconds. Herein is demonstrated that by replacing voltammetry, which measures changes in electron transfer rates indirectly, with chronoamperometry, which measures them directly, these limitations are overcome to achieve the calibration-free, sub-second-resolved measurement of specific molecules in situ in the living body.

Results and Discussion. Unlike SWV, which converts changes in electron transfer rates into a change in peak current, thus indirectly reporting on transfer kinetics, chronoamperometry measures electron transfer kinetics directly. It does so by determining the lifetimes of current transients generated in response to a stepping of the electrode's potential to values where the redox reporter will either be fully oxidized or reduced. For E-AB sensors binding to the aminoglycoside antibiotics a sufficiently negative potential was applied to drive the complete reduction of all methylene blue reporters and measured the resultant current (FIG. 3). Current decay traces were observed that are best described as the sum of two exponential processes. In the absence of their target, for example, these sensors exhibit one rapid exponential phase with a lifetime of $100 \pm 30$ µs (throughout this manuscript, errors represent the standard deviation from 5 independently fabricated sensors) and a slower one with lifetime of $6.5 \pm 0.5$ ms. The more rapid phase is attributed to charging of the double layer formed on the electrode surface at this potential bias (i.e., the migration of aqueous ions that has time-scales of µs) which remains insensitive to changes in target concentration. The slower phase, in contrast, corresponds to the faradaic reduction of methylene blue to leucomethylene blue. Upon the addition of saturating target concentrations, the second phase becomes more rapid with a lifetime of $1.20 \pm 0.01$ ms. This ~5 fold decrease in lifetime (when comparing with a sample devoid of target) agrees with a change in the proximity of the redox reporter to the electrode surface and presumably reflects a population of target-bound aptamers that transfers electrons more rapidly than the target-free aptamer.

Figure 4A:
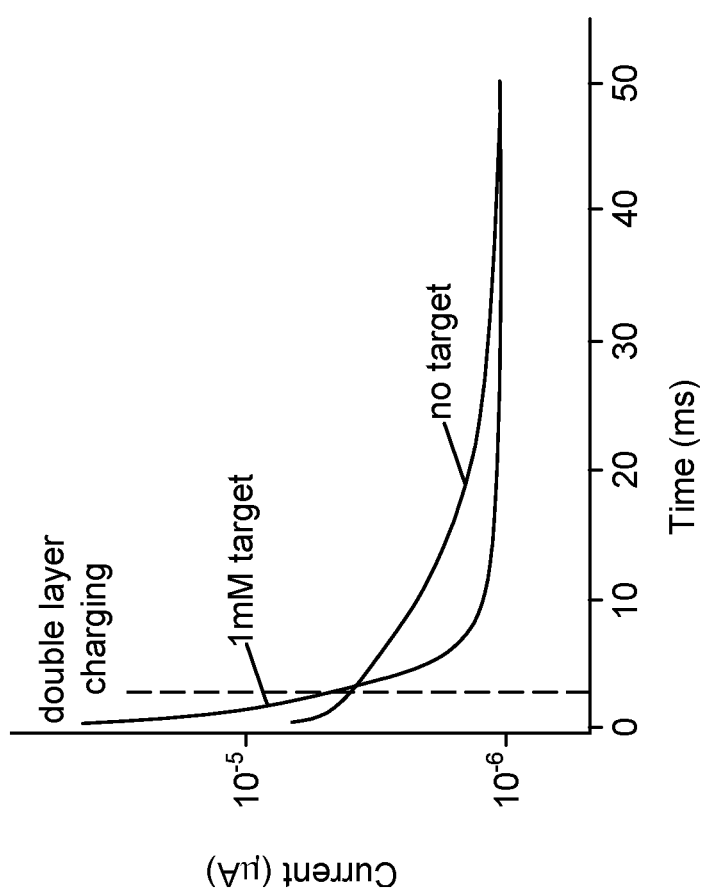
FIG. 4A, 4B, and 4C.

In theory, if the conformation dynamics of aminoglycoside-binding aptamers obey a two-state model, the relative amplitudes of the exponential phases (which reflect the populations of bound and unbound aptamers) would change monotonically with target concentration. The two-state model assumes, however, that the two exponential phases can be measured independently. This is not the case here, however, because the lifetimes of the two exponential phases are quite similar at any given concentration of target, rendering it difficult to extract their amplitudes with sufficient precision. In other words, when the kinetics of inter-conversion between the bound and unbound states of the aptamer are faster than the electron transfer event, such as is the case here, the conformational equilibrium cannot be sampled as discrete static populations. Instead, the measured lifetimes reflect a population-weighted average of the bound and unbound states. This limitation is overcome by approximating the current decay lifetime using a mono-exponential fit (FIG. 4A).

Figure 4C:
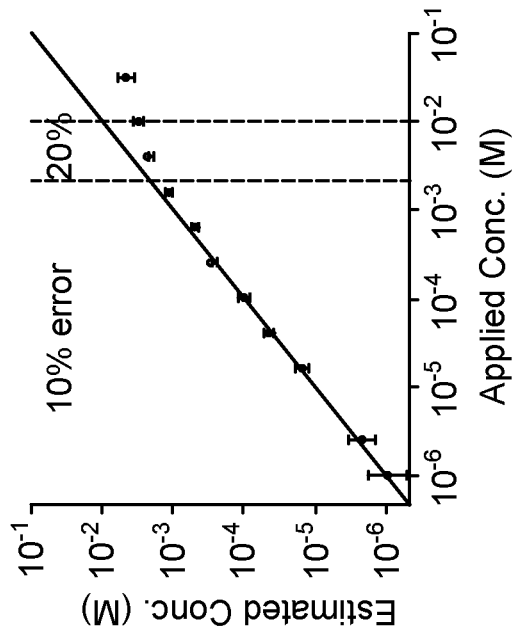
Figure 4B:
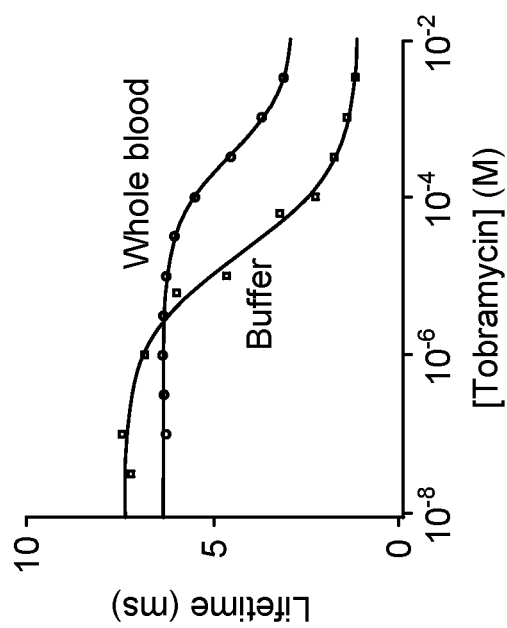

The monotonic relationship between the chronoamperometric lifetime of an E-AB sensor and the concentration of its target provides a calibration-free approach to performing E-AB measurements. That is, unlike absolute SWV peak currents, which depend on the total number of aptamers on the sensor, the lifetime of chronoamperometric decays depend only on the relative populations of the bound and unbound aptamer. Thus, once established for a given type of sensor, the lifetime-concentration relationship can be used to determine target concentrations without the need to calibrate each individual sensor. The lifetime-concentration was established relationship for aminoglycoside-detecting E-AB sensors when being used for the detection of tobramycin in vitro in flowing whole blood. Specifically, a non-linear regression of lifetime versus concentration to a Langmuir isotherm was performed (red line in FIG. 4B) and solved for concentration. A batch of five new E-AB sensors (i.e., sensors not in the initial training set) was challenged with tobramycin in whole blood, and the previously-determined Langmuir isotherm was used to convert the observed chronoamperometric lifetimes into estimated concentrations (FIG. 4C). This successfully determined concentrations of the drug with precision and accuracy of better than 10% over the range from 1 µM to 1000 µM.

In addition to being calibration-free, the use of chronoamperometrically-determined current decay lifetimes as a means of defining target concentration is also resistant to drift. Again, while SWV-interrogated E-AB sensors are selective enough to perform well in undiluted blood serum, they often exhibit severe baseline drift when deployed directly in flowing whole blood (FIG. 5A). Previously this has been corrected using square wave voltammetry approaches that involve measurements taken at multiple frequencies (FIG. 5A). Chronoamperometric lifetime measurements, in contrast, are inherently resistant to such drift; as noted above, while the total amplitude of the current transient drifts significantly (presumably due to surface reorganization of the monolayer[22]), the lifetime of its exponential decay is independent of its amplitude and thus is largely drift-free (FIG. 5B).

Figure 6B:
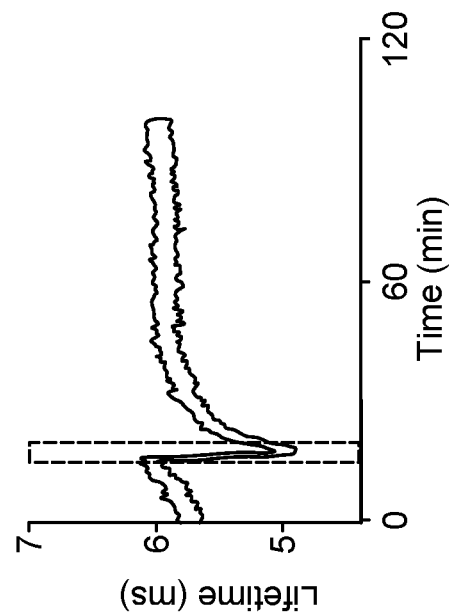
FIG. 6A, 6B, 6C, and 6D.
Figure 6A:
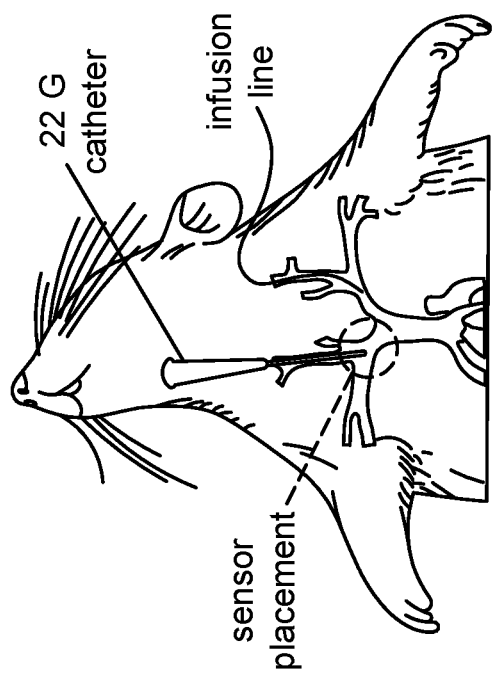
Figure 6D:
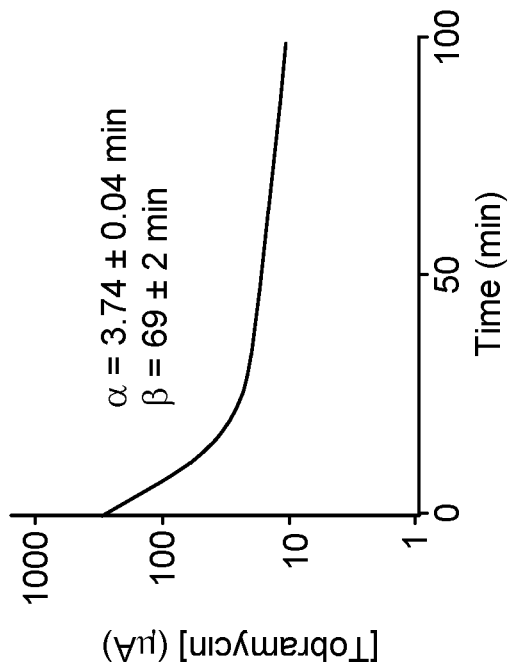
Figure 6C:
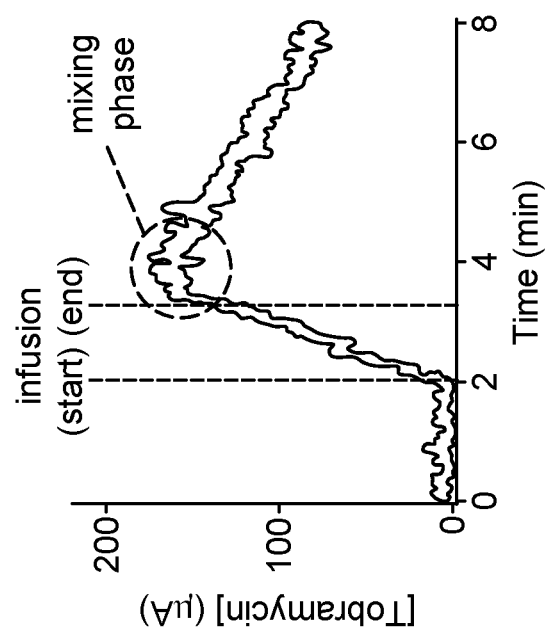

The drift-resistance of chronoamperometrically-interrogated E-AB sensors is sufficient to support continuous, real-time measurements directly in situ in the blood of live animals. Aminoglycoside-binding E-AB were fabricated sensors on 75 µm-diameter gold micro-wires, encased in 22-gauge catheters for structural support, and deployed directly in the jugular veins of live rats (FIG. 6A). The plasma pharmacokinetics of the antibiotic tobramycin were monitored following an intravenous administration of 30 mg/kg by performing continuous chronoamperometric measurements for a total of two hours (FIG. 6B). Continuous measurements were achieved by pulsing the potential of the E-AB sensors serially between −0.1 V and −0.3 V, holding each pulse with a duration of only 100 ms. Then, non-linear regression analysis was performed of the current transients generated at −0.3 V to extract current decay lifetimes in real time, and these lifetimes were converted to concentration using the previously determined Langmuir isotherm (FIG. 6C). At a time resolution of 300 ms (limited by aptamer-target binding kinetics, data acquisition and computation time) the chronoamperometric measurements resolve not only the duration of the drug infusion but also the time it takes for the drug to "mix" and reach homogeneity in the bloodstream after the end of the infusion (FIG. 6C).

The sub-second time resolution of chronoamperometrically interrogated E-AB sensors measurement of drug pharmacokinetics with unprecedented precision. The distribution, $\alpha$, and elimination, $\beta$, lifetimes of tobramycin were determined by fitting the in vivo data to a two-compartment pharmacokinetic model. The 300-ms time resolution of chronoamperometrically-interrogated E-AB sensors supports the determination of the distribution phase of the drug, $\alpha=3.74\pm0.04$ min, with more than one thousand measurement points and a calculated standard error from the fit of ~1%. Similarly, the elimination phase of the drug was determined as $\beta=69\pm2$ min with fourteen thousand measurement points, bringing down the standard error of the fit to only 3%, with much of this small deviation likely arising due to metabolic fluctuations in the animal over the course of the experiment (i.e., $\beta$ is not truly a constant). This precision is an order of magnitude improved over previous in-vivo E-AB measurements achieved using square wave voltammetry, which in turn was a large improvement over prior measurements using blood draws and ex-vivo analysis.

Herein chronoamperometric interrogation of E-AB sensors was used to achieve the calibration-free, sub-second-resolved measurement of specific small molecules directly in vivo. The unprecedented temporal resolution of this approach suggests that it could improve our understanding of rapidly fluctuating physiological events, such as drug uptake, hormone and neurotransmitter release, and the movement of drugs and metabolites within the central nervous system. The ability to perform the calibration-free measurement of specific molecules in the body in real-time could also enhance the efficiency and accuracy with which drugs are dosed, in applications ranging from therapeutic drug monitoring to long-term feedback-controlled drug delivery.

E-AB sensors are not the only class of biosensors that relies on binding-induced changes in electron transfer kinetics for the detection of analytes. Other examples include sensors that measure changes in electron transfer from solution-phase redox reporters, electron transfer changes due to binding-induced displacement of ligands, changes in the reporter's reorganizational energy, or sterically induced changes in the efficiency with which a scaffold-attached redox reporter approaches an underlying electrode surface. From this perspective, we postulate that the ability of chronoamperometry to measure electron transfer kinetics directly may also prove of value in the interrogation of these other platforms.

Methods. E-AB sensors were fabricated as follows: segments of pure gold (12 cm in length), platinum (11.5 cm) and silver (11 cm) wire, were cut to make sensors. The insulation at both ends of these wires, about 2 cm, was removed using a surgical blade to allow electrical contact. These were then soldered each to one of the three ends of a connector cable using 60% tin/40% lead rosin-core solder (0.8 mm diameter) and then attached together by applying heat to shrinkable tubing around the body of the wires, except for a small window of about 5 mm at the edge of each wire. The wires were attached in a layered fashion, with the gold wire being insulated alone first, then both gold and platinum wires together, and finally all three wires together. The purpose of this three-layer-thick insulation was to give mechanical strength to the body of the malleable probe. To prevent electrical shorts between wires, different lengths were used for each wire as described above. The sensor window (i.e., the region devoid of insulation) in the gold wire was cut to approximately 3 mm in length. The silver wire was employed as a reference electrode by first immersing it in bleach overnight to form a silver chloride film. To increase surface area of the gold working electrodes (to obtain larger peak currents) the sensor surface was roughened electrochemically via immersion in 0.5 M sulfuric acid followed by stepping the potential between $E_{initial}=0.0$ V to $E_{high}=2.0$ V vs Ag/AgCl, back and forth, for 16,000 pulses. Each potential step was of 20 ms duration with no "quiet time." To fabricate sensors an aliquot of the DNA construct was reduced for 30 min at room temperature with a 1000-fold molar excess of tris(2-carboxyethyl) phosphine. A freshly roughened probe was then rinsed in deionized water before being immersed in a solution of the reduced DNA construct at 200 nM in PBS for 1 h at room temperature. Following this the sensor was immersed overnight at 4° C. for 12 h in 20 mM 6-mercapto-1-hexanol in PBS to coat the remaining gold surface. After this the sensor was rinsed with deionized water and stored in PBS.

For the SWV measurements, the sensors were interrogated from 0.0 V to −0.5 V versus Ag/AgCl, using an amplitude of 50 mV, potential step sizes of 1-5 mV, and varying frequencies from 10 Hz to 500 Hz. All SWV measurements were performed using a three-electrode setup and with a CH Instruments™ electrochemical workstation (Austin, TX, Model 660D) using commercial Ag/AgCl reference electrodes filled with saturated KCl solution and platinum counter electrodes. For chronoamperometry, the potential of the sensors was serially stepped from −0.1 V to −0.3 V, each step for a duration of 100 ms. Current sampling was carried out every 10 µs for in vitro measurements, and every 100 µs for in vivo measurements (to reduce the number of experimental points and speed data acquisition). All chronoamperometric measurements were performed using the three-electrode E-AB sensor described above and recorded with a GAMRY™ Reference 600+ Potentiostat/Galvanostat/ZRA (Warminster, PA).

To study the behavior of chronoamperometric current decays, to measure aptamer affinity and to correlate signal gain to target concentration, sensors were interrogated by either square wave voltammetry or chronoamperometry first in flowing PBS and next in flowing heparinized bovine blood with increasing concentrations of the corresponding target. These experiments were carried out in a closed flow system intended to mimic the type of blood transport found in veins. Blood flow was achieved using a magnetic gear pump, setting flow rates to 1-10 mL min$^{-1}$ as measured by a flow meter. To construct the binding curves (titrations of aptamer with target), stock solutions of tobramycin were prepared fresh prior to measurements in PBS buffer or blood, respectively. The sensor challenge to demonstrate calibration-free behavior was performed by challenging a fresh batch of aminoglycoside-binding E-AB sensors against stock solutions made from a tobramycin reference standard.

In-vivo measurements were performed in anaesthetized rats, wherein either a silastic catheter was inserted for infusions or the E-AB sensor was placed for measurements in the jugular vein. All in vivo measurements were performed using a three-electrode setup in which the reference electrode was a silver wire coated with a silver chloride film as described above, and the counter electrode was a platinum wire. Recordings were taken for up to 3 h, with sampling rates of one point every 300 milliseconds. To obtain pharmacokinetic profiles from our real-time data non-linear regression analysis was performed using a two-compartment model to fit intravenous injections. The equation employed in the regressions was the following:

$$C_P = Ae^{-t/\alpha} - Be^{-t/\beta}$$

where $C_P$ is the measured plasma concentration, A and B are contributions of each pharmacokinetic compartment to the maximum concentration $A+B=C_{MAX}$, $\alpha$ is the first-order time constant of drug distribution and $\beta$ is the drug's elimination time constant. During the regression analysis, all variables were floating such that the best fit was determined by minimizing the squared errors.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of measuring a target species concentration in a sample by using an electrochemical sensor, the method comprising:
    deploying an electrochemical sensor such that it is exposed to the sample, wherein the electrochemical sensor comprises an electrode functionalized with a plurality of recognition elements that undergo a conformation change upon binding with the target species, wherein each of the plurality of recognition elements is functionalized with one or more redox reporters characterized by an electron transfer kinetics, wherein the conformation change of at least one of the plurality of recognition elements changes the electron transfer kinetics of at least one of the one or more redox reporters;
    applying one or more excitation pulses to the electrochemical sensor, wherein a faradaic current output is generated by each of the one or more excitation pulses, wherein the faradaic current varies in a concentration-dependent manner with the target species concentration in the sample;
    acquiring a time-resolved faradaic current data following each of the one or more excitation pulses, wherein the time-resolved faradaic current data directly measures a change of the electron transfer kinetics as a result of the binding of the target species with the electrochemical sensor;
    by the acquired time-resolved faradaic current data, calculating a value of a selected measure of current decay;
    by the value of a selected measure of current decay, calculating the concentration of the target species by application a mathematical relationship between the selected measure of current decay and the concentration of the target species in the sample.

2. The method of claim 1, wherein the electrochemical sensor comprises an electrode functionalized with a plurality of recognition elements that undergoes a conformational change upon target binding, wherein each recognition element is functionalized with one or more redox reporters.

3. The method of claim 2, wherein the recognition element comprises an aptamer.

4. The method of claim 1, wherein the sample is selected from the group consisting of whole blood, serum, saliva, urine, sweat, interstitial fluid, spinal fluid, cerebral fluid, tissue exudates, macerated tissue samples, cell solutions, intracellular compartments, water, wash water, wastewater, groundwater, food, and beverages.

5. The method of claim 1, wherein the sample comprises flowing whole blood.

6. The method of claim 4, wherein the sample is not processed prior to measurement.

7. The method of claim 4, wherein the sample is not diluted prior to measurement.

8. The method of claim 1, wherein the target species is selected from the group consisting of a small molecule drug, a metabolite, a hormone, a peptide, a protein, a carbohydrate, a nucleic acid, a lipid, a growth factor, a neurotransmitter, a nutrient, a pollutant, a pathogen-induced or pathogen-derived factor, a pathogen, and a cell.

9. The method of claim 1, wherein the selected measure of current decay is selected from the group consisting of a decay constant, an average lifetime, a half-life, and a relative amplitude.

10. The method of claim 1, wherein the selected measure of current decay is derived from an exponential fit of the time-resolved current data.

11. The method of claim 10, wherein the selected measure of current decay is derived from a monoexponential fit of the time-resolved current data.

12. The method of claim 1, wherein the selected measure of current decay is derived from a biexponential fit of the time-resolved current data.

13. The method of claim 1, wherein the mathematical relationship between the selected measure of current decay and target concentration is derived for sensors of a same class as the deployed electrochemical sensor.

14. The method of claim 1, wherein no calibration step is performed prior to or after the measurement.

15. The method of claim 1, wherein repeated measurements are obtained over hours, days, months, or longer.

16. The method of claim 15, wherein the electrochemical sensor is deployed in vivo.

17. The method of claim 16, wherein the electrochemical sensor is deployed in a human subject.

18. The method of claim 16, wherein the electrochemical sensor is deployed in a non-human animal.

19. The method of claim 1, wherein the electrochemical sensor is deployed in a point-of-care system.

* * * * *